United States Patent [19]

Grill et al.

[11] Patent Number: 5,116,749
[45] Date of Patent: May 26, 1992

[54] GAMMA-GLUTAMYLCYSTEINE TRANSFERASE

[75] Inventors: Erwin Grill; Susanne Loffler; Ernst-Ludwig Winnacker; Meinhard H. Zenk, all of Munchen, Fed. Rep. of Germany

[73] Assignee: Consortium fur Elektrochemische Industrie GmbH, Munich, Fed. Rep. of Germany

[21] Appl. No.: 373,400

[22] Filed: Jun. 30, 1989

[30] Foreign Application Priority Data

Jul. 28, 1988 [DE] Fed. Rep. of Germany ....... 3825677

[51] Int. Cl.$^5$ .................. C12N 9/10; C12N 11/00
[52] U.S. Cl. ................................ 435/193; 435/174
[58] Field of Search ........................... 435/193, 174

[56] References Cited

U.S. PATENT DOCUMENTS

| 4,710,489 | 12/1987 | Meister | 514/18 |
| 4,758,551 | 7/1988 | Meister et al. | 514/18 |
| 5,001,055 | 3/1991 | Imahori et al. | 435/89 |

Primary Examiner—David M. Naff
Assistant Examiner—Mike Mellor
Attorney, Agent, or Firm—Collard, Roe & Galgano

[57] ABSTRACT

The enzyme γ-glutamylcysteine transferase is disclosed. γ-Glutamylcysteine transferase catalyzes the transfer of γ-glutamylcysteine or γ-glutamycysteine S-derivates and is produced by extracting plant material from the families of *Apocynaceae, Asciepladaceae, Berberidaceae, Chenopodiaceae, Caryophyllacea, Dioscoreaceae, Fumariaceae, Graminaceae, Iridaceae, Leguminosae, Menispermaceae, Papveraceae, Ranunculaceae, Rosaceae, Rubiaceae, Solanaceae* or *Violaceae*, or tissue of algea (*Phycophyta*) or fungi (*Mycophyta*).

3 Claims, No Drawings

GAMMA-GLUTAMYLCYSTEINE TRANSFERASE

The present invention relates to a protein having catalytic activity. More particularly, the present invention relates to protein which catalyzes the transfer of γ-glutamylcysteine or γ-glutamylcystein S-derivatives, known as γ-glutamylcyseine transferase.

This enzyme includes the following parameters: molecular weight 95,000±10%, determined by gel filtration;
the enzyme in the natural state is a dimeric protein (molecular weight of each unit 47,000±10%);
optimum temperature 45° C.;
optimum pH=8.0;
$K_M$ at 30° C. and pH=7.8; 6.8 mM for glutathione and 1.0 mM for glutathione S-biman;
complete inhibition in the presence of ethylenediaminetetraacetic acid (EDTA), reversible after removal of EDTA and addition of heavy metal ions; and,
cofactors: heavy metal ions.

Heavy metals within the meaning of the invention are metals whose density is greater than the density of iron. Examples of such heavy metal ions are, in particular, the cations of the metals lead, tin, bismuth, titanium, manganese, cobalt, nickel, copper, silver, gold, platinum, zinc, cadmium, mercury, uranium, arsenic and selenium.

γ-Glutamylcysteine transferase can be obtained by extraction of plant material. Suitable, in principle, as plant material are both the lower and the higher plants, because the enzyme according to the invention is an enzyme of primary metabolism. Examples of plant material are:

| | |
|---|---|
| *Rauwolfia serpentina* (Apocynacae) | *Iris pallida* (Irdaceae) |
| *Asclepias syriaca* (Asclepiadaceae) | *Crotalaria cobalticola, Phaseolus vulgaris* (Leguminosae) |
| *Berberis stolonifera* (Berberidaceae) | *Cissampelos mucronata* (Menispermaceae) |
| *Beta vulgaris* (Chenpondiaceae) | *Glaucium flavum* (Papaveraceae) |
| *Silene cucubalus* (Caryophyllaceae) | *Coptis japonica* (Ranunculaceae) |
| *Helianthus annuus* (Compositae) | *Rosa canina* (Rosaceae) |
| *Dioscorea composita* (Dioscoreaceae) | *Morinda citrifolia* (Rubiaceae) |
| *Fumaria capreolata* (Fumariaceae) | *Nicotiana tabacum* (Solanaceae) |
| *Agrostis tenuis* (Graminaceae) | *Viola calaminaria* (Violaceae) | as well as: *Euglena gracillis, Fragillaria crotonensis, Navicula pelliculosa, Bumilleriopsis filiformis, Chlamydomonas reinhardii, Chlorella fusca, Monoraphidium minutum, Scenedesmus acutiformis, Stichococcus bacillaris, Sargassum muticum, Porhyridium cruentum* (Phycophyta) and *Amylostereum chailetti, Sarcosypha austriaca, Schizosaccharomyces pombe, Schizosaccharomyces versatilus, Sporobolomyces holsaticus* (Mycophyta).

Preferably used are the higher plants *Silene cucubalus* and *Crotalana cobalticola*, as well as *Schizosaccharomyces pombe* as fungus.

Preferably employed as plant material are cell cultures of the said plants. However, it is also possible to employ the differentiated plants or parts of plants, including the roots, for obtaining the enzyme according to the invention.

The extraction of the plant material is carried out using methods with which it has also previously been possible hitherto to extract enzymes from plants. The procedure is customarily such that, initially, the cell structure of the plants or of the corresponding cell cultures is destroyed. For this purpose, the plant material is expediently frozen, for example at the temperature of liquid nitrogen, where appropriately comminuted, and finally taken up in an aqueous preparation of pH 6 to pH 10. Used as aqueous preparations are, in particular, the buffer solutions suitable for the foregoing pH range, for example, a phosphate buffer. It is possible, where appropriate, after removal of non-disrupted plant material to concentrate the proteins by protein precipitation and subsequent gel filtration. The protein precipitation is carried out by addition of an electrolyte (especially ammonium sulfate). The precipitated proteins are subsequently taken up in an aqueous buffer solution (pH=6 to 10) and subjected to a gel filtration. The gel filtration achieves both removal of salts and a fractionation on the basis of molecular size of the protein mixture which is present. Used for further working up is that portion of the eluate from the gel filtration which contains the proteins of molecular weight >40,000. The subsequent purification steps include further chromatographic separation of the protein mixture on a hydrophobic column matrix (for example phenyl-Sepharose, Pharmacia, Freiburg), on hydroxyapatite (Biorad) and on ion exchangers (for example diethylaminoethylcellulose). The choice of eluate in this connection is always based on the checks of enzyme activity. If desired, it is also possible to use other or additional separation methods such as, for example, electrophoresis, isoelectric focusing and the like.

The working-up procedures described above are carried out in an aqueous system especially in buffer solutions of pH 6 to 10, especially pH 7 to 9, at temperatures of, preferably, 4° C. to 15° C.

The preparations obtained by the process according to the invention are aqueous or, where appropriate, freeze-dried and exhibit an enzymatic activity corresponding to a content of γ-glutamylcysteine transferase.

Hence the subject of the invention is a composition having enzymatic activity and containing γ-glutamylcysteine transferase.

The enzyme according to the invention can frequently be advantageously employed in an immobilized state. For this purpose, the enzyme is physisorbed or chemisorbed on carrier materials in a conventional manner. Examples of carrier materials are alginates and, functional groups carrying agaroses, cellulose, polyacrylic resins (with, for example, oxirane groups), glasses and silicates.

The enzyme according to the invention catalyzes the transfer of γ-glutamylcysteine or of γ-glutamylcystene S-derivatives.

Hence the subject matter of the present invention further includes a process for enzymatic polymerization, which comprises reacting compounds of the general formula (I)

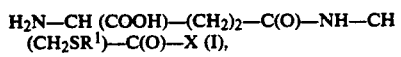

wherein,
R[1] denotes hydrogen, an alkyl or an aryl radical; and
X denotes a group of the general formula NHR[2] with R[2] representing hydrogen, an alkyl or an aryl radical, or NH—CH (R[3])—COOH with the proviso that R[3] represents the appropriate radical of all naturally occurring amino acids of the formula NH₂CH (R³) COOH,
in the presence of γ-glutamylcysteine transferase. Preferably, R¹ represents hydrogen, 2,4-dinitrophenol or biman radical, R² represents hydrogen, cabroxymethyl, 4-nitrophenyl or naphthyl or radical and R³ represents hydrogen, hydroxyl, methyl or benzyl radical.

Examples of compounds to be polymerized according to the invention are glutathione, homoglutathione and γ-glutamylcysteinylamide.

The process, according to the invention, results in polymers of the general formula II

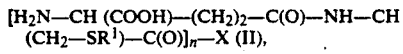

wherein the degree of polymerization, n, is an integer from 2 to 20.

Examples of such polymers are phytochelatin with R¹ representing hydrogen and X representing NHCH₂COOH; homo-phytochelatin with R¹ representing hydrogen and X representing NHCH₂CH₂OH, poly(glutamylcysteine) with R' representing hydrogen and X representing OH and poly(glutamylcysteine) amide with R¹ representing hydrogen and X representing NH₂.

The reaction temperatures are preferably 10° to 70° C., especially 25 to 50° C.

The procedure preferably utilizes an aqueous enzyme preparation, or a preparation in which the enzyme is present in an immobilized state, which is added to an aqueous preparation of substances of the general formula I of pH 6 to 10, especially 8.0, preferably in the presence of the above-mentioned heavy metal ions in a concentration of 0.1 µmol/l to 10 mmol/l, especially 10 to 500 µmol/l. Thereafter, the mixture is stirred.

The amount of enzyme employed, based on the amount of substrate, is not, per se, critical and is adjusted on the basis of the desired product conversion. Normally employed per 1 mole of substrate to be employed are amounts of enzyme in the range from 1 to 50 g, especially 15 to 20 g.

The course of the reaction is followed, for example, by high-pressure chromatography with underivatized or derivatized reaction products.

The reaction products of the general formula (II) are used for detoxifying heavy metals.

The present invention will now be described with reference being made to the following examples. It should, however, be recognized that the following examples are intended to be merely illustrative of the present invention and are not intended as defining the scope thereof.

EXAMPLE 1

Preparation of γ-glutamylcysteine transferase 500 g of a cell culture of Silene cucubalus, which had been frozen with liquid nitrogen, were stirred in 250 ml of an aqueous trihydroxymethylaminomethane-HCl buffer solution (50 millimolar, pH=8.5) containing 10 mM mercaptoethanol for 20 minutes. The resulting cell homogenate was subsequently filtered off and centrifuged. 85 g/l of solid ammonium sulfate were added to the supernatant. The protein precipitate produced by this was removed by centrifugation, and the proteins in the supernatant were bound to a phenyl-Sepharose column (2.5×20 cm, Pharmacia, Freiburg). The column wa washed with 0.2 l of ammonium sulfate solution (10 mM tris-HCl, pH=7.8, 86 g of ammonium sulfate per liter, 10 mM mercaptoethanol), and subsequently bound protein was eluted with a solution composed of 10 mM tris-HCl, 10 mM mercaptoethanol and 10% ethylene glycol (pH=7.8). The elutate was pumped onto a hydroxyapatite column (1.5×11.5 cm; Biorad, Munich) which had been equilibrated with a solution of 10 mM potassium phosphate buffer, pH=7.8, 10 mM mercaptoethanol, 10 mM NaCl and 0.5 mM MgCl₂. The column was washed with 100 ml of the buffer, and subsequently the γ-glutamylcysteine transferase was eluted by a stepped gradient composed of from 20 to 100 mM potassium phosphate and 10 mM mercaptoethanol. The active fraction from this elution was loaded onto an ion exchanger ((Anion)MonoQ, Pharmacia, Freiburg) after the potassium phosphate had been diluted to at least 1/10 of the initial concentration by ultrafiltration (Amicon, Düren) and washing the retentate with a buffer composed of 20 mM tris-HCl buffer, pH=8.5, 10 mM NaCl, 10 mM mercaptoethanol and 0.5 mM MgCl₂. Elution was carried out with a 10-350 mM NaCl gradient in the above-mentioned buffer. The active fraction from this elution was adjusted to 10% by weight ammonium sulfate by addition of a 50% strength ammonium sulfate solution in 10 mM tris-HCl, pH=7.8, pumped onto a phenyl-Suparose column (Pharmacia, Freiburg) and eluted with a linear gradient composed of A 86 g of ammonium sulfate per liter in 10 mM tris-HCl, 10 mM mercaptoethanol, 10 mM NaCl and 0.5 mM MgCl₂, and B 10 mM tris-HCl, 10 mM mercaptoethanol, 10 mM NaCl, 0.5 mM MgCl₂ and 10% ethylene glycol. The active fraction from this elution was subjected to a gel filtration on SW 3000 (LKB, now Pharmacia, Freiburg) in 50 mM β-alanine, 10 mM histidine, pH 6.6, 10 mM mercaptoethanol and 0.5 mM MgCl₂. The active fraction had an activity of 1 nkat/mg of protein. The yield was 10%.

As an alternative, the following purification process can be employed after the hydroxyapatite column:

10% glycerol was added to the active fractions which were then loaded onto an Aca 34 column (Pharmacia, Freiburg) and eluted with 10 mM tris-HCl buffer, pH 7.8 and 10 mM mercaptoethanol. The active fractions were applied to an anion exchanger QAE FF (Pharmacia, Freiburg) and eluted with a KCl gradient, 150-400 nM KCl. The active fractions were adjusted to 10% by weight ammonium sulfate, by addition of powdered ammonium sulfate, pumped onto a phenyl-Superose column (Pharmacia, Freiburg) and eluted with a linear gradient composed of A 85 g of ammonium sulfate per liter in 10 mM tris-HCl buffer and 10 mM mercaptoethanol, and B 10 mM tris-HCl buffer and 10 mM mercaptoethanol. The active fractions were dialyzed against 10 l of potassium phosphate buffer pH 8.0 (25 mM) and subsequently loaded onto a chelating Sepharose column (Phamacia, Freiburg) which was loaded with Zn²⁺. Elution was carried out with 50 mM imidozole in 25 mM potassium phosphate buffer pH 8.0. The active fraction had a specific activity of 1 nkat/mg of protein.

EXAMPLE 2

Preparation of immobilized γ-glutamylcysteine transferase 6 ml of an enzyme preparation of γ-glutamylcysteine transferase in an aqueous, 10 mM NaCl, 0.1 molar, pH=7.8) with an enzyme activity of 1.2 nkat/mg and a protein content of 1.02 mg/ml were introduced into 50 ml of a 5% by weight aqueous alginate solution, while stirring. The enzyme-containing alginate solution was subsequently added dropwise to 500 ml of a 0.1 molar aqueous calcium chloride solution at 5° C., while stirring. A product in the form of beads of immobilized enzyme on calcium alginate was obtained and was then washed with the above-mentioned buffer. The product had an enzyme activity of 0.32 nkat/mg of protein.

EXAMPLE 3

Enzymatic polymerization of glutathione

20 μmol of a 10 mM $Cd^{2+}$ solution were added continuously to 50 ml of an enzyme preparation of γ-glutamylcysteine transferase in an aqueous solution of tris-HCl (0.1 molar, pH 7.8), 15 mM glutathione, 10 mM NaCl with an enzyme activity of 1.1 nkat/mg of protein and a protein content of 0.26 mg/ml over one hour. After one hour, 15 mg of phytochelatins with a $CD^{2+}$ content of 18.2% by weight were obtained. The $Cd^{2+}$ was removed by precipitation with gaseous hydrogen sulfide.

While only several examples of the present invention have been described, it will be obvious to those of ordinary skill in the art that many modifications may be made to the present invention without departing from the spirit and scope thereof.

What is claimed is:

1. A substantially purified γ-Glutamylcysteine transferase having the following characteristics comprising:
   a) molecular weight 95,000±10%, determined by gel filtration; enzyme in the form of a dimeric protein (monomer 47,000±10%);
   b) optimum temperature 45° C.;
   c) optimun pH=8.0;
   d) $K_M$ at 30° C., and pH=7.8, 6.8 mM for glutathione and 1.0 mM for glutathione S-biman;
   e) complete inhibition in the presence of ethylenediaminetetraacetic acid (EDTA), reversible after removal of EDTA and addition of heavy metal ions; and
   f) cofactors being heavy metal ions.

2. γ-glutamylcysteine transferase according to claim 1, wherein said γ-glutamylcysteine transferase is in an immobilized state.

3. A substantially purified γ-Glutamylcysteine transferase obtainable by isolation of the γ-glutamylcysteine transferase from plant material selected from the group consisting of:
   material from the family *Apocynaceae;*
   material from the family *Asclepiadaceae;*
   material from the family *Berberidaceae;*
   material from the family *Chenopodiaceae;*
   material from the family *Caryphyllacea;*
   material from the family *Compositae;*
   material from the family *Dioscoreaceae;*
   material from the family *Fumariaceae;*
   material from the family *Graminaceae;*
   material from the family *Iridaceae;*
   material from the family *Leguminosae;*
   material from the family *Menispermaceae;*
   material from the family *Papveraceae;*
   material from the family *Ranunculacear;*
   material from the family *Rosaceae;*
   material from the family *Rubiaceae;*
   material from the family *Solanaceae;*
   material from the family *Violaceae;*
   tissue of algae *Phycophyta;*
   fungi *Mycophyta;*
   and a combination thereof.

* * * * *